US008409865B2

(12) United States Patent
Calton et al.

(10) Patent No.: US 8,409,865 B2
(45) Date of Patent: Apr. 2, 2013

(54) METHODS AND KITS FOR THE DETERMINATION OF THE PRESENCE AND QUANTITY OF VITAMIN D ANALOGS IN SAMPLES

(75) Inventors: Lisa Jane Calton, Stockport (GB); Kendon Stuart Graham, Millis, MA (US)

(73) Assignee: Waters Technologies Corp., Milford, MA (US)

( * ) Notice: Subject to any disclaimer, the term of this patent is extended or adjusted under 35 U.S.C. 154(b) by 189 days.

(21) Appl. No.: 12/918,924

(22) PCT Filed: Feb. 20, 2009

(86) PCT No.: PCT/US2009/034606
§ 371 (c)(1),
(2), (4) Date: Oct. 20, 2010

(87) PCT Pub. No.: WO2009/108571
PCT Pub. Date: Sep. 3, 2009

(65) Prior Publication Data
US 2011/0195513 A1    Aug. 11, 2011

Related U.S. Application Data

(60) Provisional application No. 61/031,033, filed on Feb. 25, 2008.

(51) Int. Cl.
*G01N 33/50* (2006.01)
*G01N 1/10* (2006.01)
*G01N 30/72* (2006.01)

(52) U.S. Cl. .......... 436/131; 422/430; 436/71; 436/127; 436/161; 436/173; 436/174; 436/177; 436/178

(58) Field of Classification Search .................. 422/430; 436/71, 127, 131, 161, 173–174, 177–178
See application file for complete search history.

(56) References Cited

U.S. PATENT DOCUMENTS

| 5,135,875 | A | * | 8/1992 | Meucci et al. | ................. 436/518 |
| 5,821,020 | A | | 10/1998 | Hollis | |
| 2003/0199001 | A1 | | 10/2003 | Pitt et al. | |
| 2006/0214104 | A1 | | 9/2006 | Pope et al. | |
| 2006/0228809 | A1 | * | 10/2006 | Clarke et al. | ................. 436/173 |
| 2007/0087446 | A1 | | 4/2007 | Gebler et al. | |
| 2007/0243383 | A1 | | 10/2007 | Jiang et al. | |
| 2009/0137056 | A1 | * | 5/2009 | Holmquist et al. | ........... 436/127 |
| 2010/0285603 | A1 | * | 11/2010 | Kobold et al. | ................. 436/131 |

FOREIGN PATENT DOCUMENTS

| EP | 0471295 | 2/1992 |
| GB | 1576524 | 10/1980 |
| GB | 2269898 | 2/1994 |
| WO | 2006107992 | 10/2006 |

OTHER PUBLICATIONS

Watson, D. et al, Biomedical Chromatography 1991, 5, 153-160.*
Zhang, H. et al, Analytical Chemistry 1999, 71, 3955-3964.*
Kissmeyer, A.-M. et al, Journal of Chromatography A 2001, 935, 93-103.*
Walker, V. et al, Anals of Clinical Biochemistry 2002, 39, 464-477.*
Wyndham, K. D. et al, Analytical Chemistry 2003, 75, 6781-6788.*
Heudi, O. et al, Journal of Chromatography A 2004, 1022, 115-123.*
Vogeser, M. et al, Clinical Chemistry 2004, 50, 1415-1417.*
Tsugawa, N. et al, Analytical Chemistry 2005, 77, 3001-3007.*
Maunsell, Z. et al, Clinical Chemistry 2005, 51, 1683-1690.*
Guo, T. et al, Clinica Chimica Acta 2006, 372, 76-82.*
Capote et al., "Identification and determination of fat-soluble vitamins and metabolites in human serum by liquid chromatography/triple quadrupole mass spectrometry with multiple reaction monitoring"; Rapid Communications in Mass Spectrometry, V21, No. 11, (Jun. 15, 2007), 1745-1754.
Thomas M. Annesley et al, Simple Extraction Protocol for Analysis of Immunosuppressant Drugs in Whole Blood, Clinical Chemistry, 2004, pp. 1845-1848, vol. 50, No. 10.
Ruth D. Coldwell et al, Gas Chomatography-Mass Spectrometry and the Measurement of Vitamin D Metabolites in Human Serum or Plasma, Steroids, 1987, pp. 155-196, vol. 49.

* cited by examiner

*Primary Examiner* — Arlen Soderquist
(74) *Attorney, Agent, or Firm* — McCarter & English, LLP; Deborah M. Vernon

(57) ABSTRACT

Embodiments of the present invention are directed to methods and kits for determining the presence or absence, and the amount if present, of vitamin D analogs in samples. One embodiment of the present method for detecting the presence or absence of vitamin D analogs in a sample comprises the steps of adding an effective amount of a multiple charge cationic agent to the sample to form a cationic treated sample. The effective amount of a multiple charge cationic agent enhances the signal from vitamin D analogs upon analysis by mass spectroscopy.

17 Claims, 1 Drawing Sheet

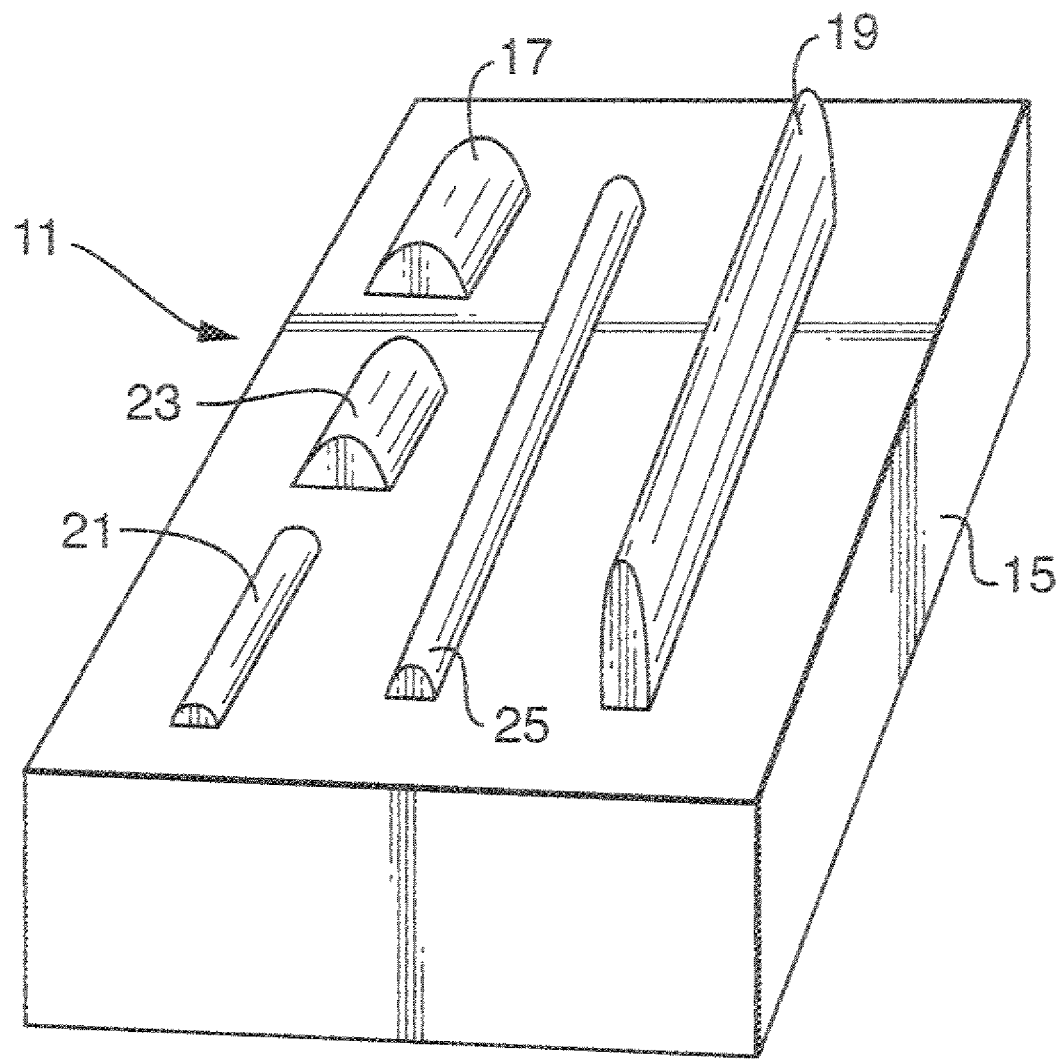

METHODS AND KITS FOR THE DETERMINATION OF THE PRESENCE AND QUANTITY OF VITAMIN D ANALOGS IN SAMPLES

CROSS REFERENCE TO RELATED APPLICATION

This application claims priority from U.S. Provisional Patent Application No. 61/031,033, filed Feb. 25, 2008. The entire contents of these applications are incorporated herein by reference.

STATEMENT REGARDING FEDERAL SPONSORSHIP

The inventions presented herein were not supported by Federal grants or funding.

FIELD OF THE INVENTION

The present invention relates to the field of diagnostics wherein it is desirable to detect or monitor the presence and amounts of vitamin D and vitamin D analogs in samples

BACKGROUND OF THE INVENTION

Vitamin D deficiency is a problem for the elderly and in individuals with severe liver or kidney disease. Deficiencies may also be noted in individuals who experience little exposure to the sun or have poor nutrition.

Vitamin D refers to a group of closely related compounds of which two are of primary importance in humans, vitamin $D_2$ and vitamin $D_3$. Vitamin $D_2$, ergocalciferol, is depicted in the chemical formula 1 below:

FORMULA 1

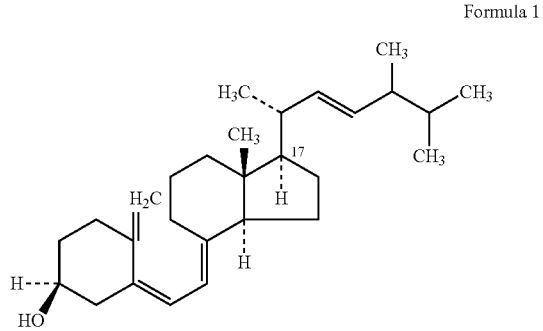

Formula 1

Vitamin $D_3$, cholecalciferol, is depicted in the chemical formula 2 below:

FORMULA 2

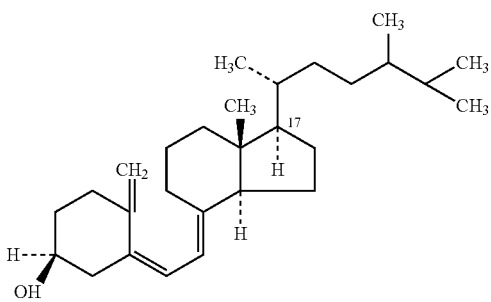

Formula 2

Vitamin $D_3$ is synthesized in the light mediated reactions in the skin and in humans is the most active form. In the liver, vitamin $O_2$ and vitamin $D_3$ are converted to 25-hydroxyvitamin $D_2$ and 25-hydroxyvitamin $D_3$. In the kidney, 25-hydroxyvitamin $D_2$ and 25-hydroxyvitamin $D_3$ are converted to 1,25 dihydroxyvitamin $D_2$ and 1,25 dihydroxyvitamin $D_3$.

Vitamin D deficiencies are normally treated with vitamin $D_2$. It is desirable to have an accurate and reproducible method to detect and monitor vitamin D levels and vitamin $D_2$ levels in biological samples to evaluate vitamin deficiencies and treatments. This document will refer to all closely related vitamin D compounds and their precursors and metabolites as vitamin D analogs. And, when greater chemical specificity is required, the chemical species will be identified by the term vitamin $D_2$ or vitamin $D_3$.

SUMMARY OF THE INVENTION

Embodiments of the present invention are directed to methods and kits for determining the presence or absence, and the amount if present, of vitamin D analogs in samples. One embodiment of the present method for detecting the presence or absence of vitamin D analogs in a sample comprises the steps of adding an effective amount of a multiple charge cationic agent to the sample to form a cationic treated sample. The effective amount of a multiple charge cationic agent enhances the signal of vitamin D analogs upon further analysis by mass spectroscopy. Next, the cationic treated sample is subjected to centrifugation to form a supernatant. This supernatant is loaded on separation means for separating the Vitamin D analogs from each other non-Vitamin D compositions, to form an analyte solution. The analyte solution is placed on an analytical chromatography media to forming an eluant in which the vitamin D analogs separated from each other and non-vitamin D compounds. The eluent has vitamin D analogs in the event the vitamin D analogs are present in the sample; and, are detected by mass spectroscopy. As used herein, the term "sample" refers to any material which it is desirable to evaluate. These materials will typically be of biological origin in the form of tissues or fluids. It is particularly desirable to determine blood, plasma or serum concentrations of vitamin D analogs. As used herein, the term "loaded" means placed onto in a manner in which one can separate different compounds. The term "eluted" is used to mean taking off or removing from. That which is taken off a chromatographic media is known as the "eluant".

As used herein, the term "separation means" refers to the group comprising liquid/liquid extraction, solid phase extraction and protein precipitation. In solid phase extraction the supernatant is loaded on a preparatory chromatographic media. The vitamin D analogs are eluted from the preparatory chromatographic media to form an analyte solution. The analyte solution having vitamin D analogs, in the event the vitamin D analogs are present in the sample, is further processed by placing on the analytical column having an analytical chromatography media.

As used herein, the term "liquid/liquid extraction" refers to the process of extraction by adding an aliphatic solvent to the aqueous solution comprising the supernatant. The aliphatic solvent and supernatant are mixed and separated to form an analyte solution. As used herein, an aliphatic solvent is a comprised of organic molecules having one to twelve carbons.

As used herein, the term "protein precipitation" refers to the process of placing a precipitating agent with the supernatant and separating the protein precipitants from the aqueous solution to form an analyte solution upon settling or, more commonly, further centrifugation. Precipitation agents comprise high concentrated salt solutions and alcohols, such as methanol, ethanol, propanol, butanol and the like.

One embodiment of the present invention features a multiple charge cationic agent selected from the group comprising metal sulfate salts. One preferred metal sulfate salt is zinc sulfate.

A preferred preparatory chromatographic media is a polymeric media with a hydrophilic and hydrophobic component. This chromatographic media is preferably held in a suitable container such as a column, cartridge or multi-well extraction device. A multi-well extraction device such as a 96 well plate is preferred for off line preparatory processing and a column or cartridge is preferred for on-line preparatory processing.

Preferably, the sample receives a known amount of a labeled vitamin D analog. The labeled vitamin D analog facilitates the identification of mass spectral peaks with the desired analyte. And, the labeled vitamin D analogs facilitate quantification by allowing comparison to be made between peak areas with the known quantity of labeled vitamin D analog to the unknown vitamin D analog. A preferred labeled vitamin D analog is selected from the group comprising deuterated vitamin D analogs. For example, if it is desired to identify and quantitate vitamin $D_2$ or vitamin $D_3$ analogs, a deuterated 25(OH) vitamin $D_3$ and deuterated 25(OH) vitamin $D_2$ composition is preferred.

Preferably, the method further comprises the step of drying the analytical solution and reconstituting such solids in methanol and water to form a reconstituted sample. Preferably, this reconstituted sample is chromatographically separated with an analytical chromatographic media to form an eluant. This eluant is directed to a mass spectrometer.

A preferred analytical chromatographic media is a bridged ethyl hybrid composition. This analytical chromatographic media is preferably held in an analytical column. Analytical columns are high performance columns which operate at pressures of between 1,500 and 15,000 psi. A preferred high performance column operates at pressures of 6,000 to 15,000 psi.

A further embodiment of the present invention features a kit for detecting the presence or absence of Vitamin D analogs in a sample. The term kit is used to mean an assembly of parts, components and reagents for performing a method. The kit typically will comprise packaging to hold the assembly and instructions. Embodiments of the present invention directed to a kit comprise an effective amount of a multiple charge cationic agent, and instructions for its use in a method for determining the presence or absence or quantity of a vitamin D analog. In the method, an effective amount of a multiple charge cationic agent is added to the sample to form a cationic treated sample. The effective amount of a multiple charge cationic agent enhances the signal of a mass spectrometer after centrifugation. The treated sample is centrifuged to form a supernatant. This supernatant is loaded on separation means for separating said vitamin D analogs from each other non-vitamin D compositions to form an analyte solution. The analyte solution is placed on an analytical chromatography media for forming an eluant having the vitamin D analogs separated from each other and non-vitamin D compounds. The eluent is placed in a mass spectrometer and the presence or absence or the quantity of vitamin D analogs in the sample is detected by mass spectroscopy.

In the event the sample is serum, the kit preferably comprises pipette for handling fluids. Kits directed to the analysis of solid tissue samples preferably comprise solutions for solubilizing the tissues.

One preferred multiple charge cationic agent is selected from the group comprising metal sulfate salts, such as zinc sulfate.

One preferred kit comprises separation means. The separation means comprises at least one selected from the group comprising liquid/liquid extraction, solid phase extraction and protein precipitation and such kit comprises such separation means.

For example, wherein solid phase extraction is performed by loading the supernatant on a preparatory chromatographic media and eluting the vitamin D analogs from the preparatory chromatographic media to form the analyte solution; the kit contains the preparatory chromatographic media. The preparatory chromatographic media is preferably contained within a solid phase extraction device such as single or multiple well devices for off line extractions, and columns and cartridges for on line work. Multiple well devices are commonly sold with wells in multiples of 96. A preferred preparatory chromatographic media for receiving the supernatant is a polymeric media with a hydrophilic and hydrophobic component. A preferred solid phase extraction device for off-line extraction is a well device or multi-well device.

In the event liquid/liquid extraction is performed by adding an aliphatic solvent and mixing and separating said aliphatic solvent from an aqueous solution to form an analyte solution, the kit comprises such an aliphatic solvent.

In the event protein precipitation is performed by placing mixing a precipitating agent with the supernatant and separating said protein precipitants from the aqueous solution to form an analyte solution, the kit comprises such precipitating agent.

Preferably, the kit comprises a known amount of a labeled vitamin D analog to facilitate quantification by mass spectroscopy. A preferred labeled vitamin D analog is selected from the group comprising deuterated vitamin D analogs. For example, if the analyte was 25(OH) vitamin $D_3$ and 25(OH) vitamin $D_2$, a preferred labeled vitamin D analog would comprise deuterated 25(OH) vitamin $D_3$ and deuterated 25(OH) vitamin $D_2$ Preferably, the kit further comprises an analytical chromatographic media. The analytical chromatographic media is preferably contained in an analytical column and the analytical solution is dried and reconstituted to form a reconstituted sample. This reconstituted sample is directed to the analytical chromatographic media to form an eluant. The eluant is mass analyzed by a mass spectrometer. A preferred second chromatographic media is a bridged ethyl hybrid material.

Further features and advantages of the present invention will be recognized by those skilled in the art upon viewing the drawing and reading the detailed description below.

BRIEF DESCRIPTION OF THE DRAWINGS

FIG. 1 depicts a kit embodying features of the present invention.

DETAILED DESCRIPTION OF THE INVENTION

Embodiments of the present invention will be described in detail with respect to methods and kits for determining the presence or absence, and the amount if present, of vitamin D analogs in samples. Although the term "sample" is used broadly, the present discussion will feature materials of biological origin in the form of tissues or fluids. And, in particular, the present discussion and example will be directed to blood serum and preferred steps with the understanding that certain steps and materials may be altered or modified. Embodiments of the present invention can be used to determine clinical blood concentrations of vitamin D analogs for the purpose of diagnosing deficiencies or overdosing of vitamin supplements.

Turning first to the method, the method comprises the steps of adding an effective amount of a multiple charge cationic agent to the sample, blood serum, to form a cationic treated sample. In the event the sample is presented as whole blood, individuals skilled in the art know to process the whole blood sample to obtain blood serum by spinning out the blood cells to form a blood plasma and precipitating blood proteins to form a serum. A serum sample may be of any volume; however, small volumes of approximately 200 microliters are common. The effective amount of a multiple charge cationic agent removes or facilitates removal of non-vitamin D compositions from the sample upon centrifugation.

A preferred multiple charge cationic agent selected from the group comprising metal sulfate salts such as zinc sulfate. Zinc sulfate is available from several vendors. The multiple charge cationic agent is added to the sample to a final concentration of between 0.01 to 1 M and, more preferred, 0.05 to 0.5 M.

Preferably, the sample receives a known amount of a labeled vitamin D analog. The labeled vitamin D analog is preferably added to the sample; however, it is possible to calibrate the mass spectrometer with separate runs of a calibration solution with known amounts of labeled vitamin D analogs. The labeled vitamin D analog facilitates the identification of mass spectral peaks with the desired analyte. And, the labeled vitamin D analogs facilitate quantification by allowing comparison to be made between peak areas with the known quantity of labeled vitamin D analog to the unknown vitamin D analog. A preferred labeled Vitamin D analog is selected from the group comprising deuterated vitamin D analogs. For example, if it is desired to identify and quantitate vitamin $D_2$ or vitamin $D_3$ analogs, a deuterated 25(OH) vitamin $D_3$ and deuterated 25(OH) Vitamin $D_2$ composition is preferred.

A preferred solvent for the serum vitamin D analogs and the calibration labeled vitamin D analogs is methanol. Thus, the serum, an aqueous mixture is combined with two times the volume of methanol containing 10 ng/mL $d_6$ 25(OH) vitamin $D_3$.

The multiple charge cationic agent is thoroughly mixed by vortexing for a suitable period of time, usually 5 to 180 seconds, and allowed to stand for another period of between five seconds to ten minutes to form the cationic treated sample.

Next, the cationic treated sample is subjected to centrifugation to form a supernatant. Although the inventors do not wish to be bound to any particular theory, it is believed that the multiple charge cationic agent forms complexes with the non-vitamin D compounds remaining in the serum. These complexes have less solubility and settle during centrifugation to form a supernatant that has compositions, which could possibly interfere with the detection of vitamin D compounds, removed. In the alternative, or additionally, the multiple charge cationic agent may alter proteins to which the vitamin D analogs are bound such that bound vitamin D analogs are displaced from the protein. The supernatant forms upon centrifugation between two to thirty minutes at 600 to 26,000 rpm, and, more preferably, five to ten minutes at 6000 to 20,000 rpm.

This supernatant is loaded separation means. For example, where it is desired to perform a solid phase extraction, the supernatant is loaded on a preparatory chromatographic media for separating the vitamin D analogs from each other non-vitamin D compositions. A preferred preparatory chromatographic media is a polymeric media with a hydrophilic and hydrophobic component. One preferred polymeric media is sold under the trademark OASIS® HLB (Waters Corporation (Milford, Mass.).

This preparatory chromatographic media is preferably held in a suitable container such as a column, cartridge or multi-well extraction device. A multi-well extraction device such as a 96 well plate is preferred for off line preparatory processing and a column or cartridge is preferred for on-line preparatory processing. A 96 well plate is sold with 30 mg of sorbent under the mark OASIS® HLB.

Sorbents are normally conditioned in a manner known in the art prior to loading the supernatant. Conditioning is determined, in part, by the nature of the sorbent, the manner in which the analyte will be eluted and the solvent in which the analyte is dissolved. The polymeric sorbent in the 96 multi-well device described herein is conditioned with 1 mL ethyl acetate, 1 mL methanol and equilibrated with 1 mL water, prior to loading.

After the sorbent has been conditioned and the supernatant loaded, the sorbent is washed to remove potentially interfering compounds. Thus, the sorbent is washed twice; first, with 1 mL of 5% methanol/water solution and, next, with 1 mL 80% methanol/water solution.

The vitamin D analogs are eluted from the preparatory chromatographic media to form a analyte solution. The analyte solution has vitamin D analogs in the event the vitamin D analogs are present in the sample. In the event a labeled vitamin D analog has been added to the sample, the labeled vitamin D analogs will also be present. The vitamin D analogs, both labeled and unlabeled are eluted with two volumes of 500 uL ethyl acetate.

Preferably, the analyte is dried and reconstituted to form a reconstituted sample. For example, the analyte solution is dried under nitrogen or some other inert gas at elevated temperatures, for example 50 degrees centigrade. Preferably, such reconstituted sample is formed in methanol and water. A preferred solution is 70/30 methanol/water. A typical volume is 200 microliters.

The reconstituted sample is chromatographically separated with a analytical chromatographic media to form an eluant. This eluant is directed to a mass spectrometer.

A preferred analytical chromatographic media is a bridged ethyl hybrid composition. This second chromatographic media is preferably held in an analytical column. Analytical columns are high performance columns which operate at pressures of between 1,000 and 15,000 psi. A preferred high performance column operates at pressures of 6,000 to 15,000 psi. A preferred column is sold under the trademark ACQUITY® BEH 2.1×50 mm, C8, 1.7 micron particles (Waters Corporation, Milford, Mass.). A preferred instrument for receiving such column is an ACQUITY® HPLC® chromatography system (Waters Corporation, Milford, Mass.).

The vitamin D analogs and labeled vitamin D analogs are eluted with a gradient comprised of two solutions. The first solution is water with 2 mM ammonium acetate with 0.1% formic acid, sometimes referred herein as "mobile phase A". The second solution is methanol with 2 mM ammonium acetate with 0.1% formic acid, sometimes referred herein as "mobile phase B". The first solution is used as a weak wash solvent and the second solution is used a strong wash solvent for the system.

A gradient is established over a period of time. One preferred gradient starts at approximately 25% mobile phase A and 75% mobile phase B and to 75% mobile phase A and 25% mobile phase B over six minutes with a flow rate of 0.35 mL/minute and an injection volume of 20 microliter (PLNO, 50 microliter loop and 250 microliter sample syringe. The retention time of 25(hydroxy)vitamin $D_2$ is 3.48 minutes, 25(hydroxyl)vitamin $D_3$ is 3.3 minutes and $d_6$ 25(hydroxyl) vitamin $D_3$ is 3.3 minutes.

The vitamin D analogs are detected by mass spectroscopy. Mass Spectrometer are available from several venders under different trademarks. A preferred mass spectrometer is sold as the WATERS® TQD, a tandem quadrupole detector mass spectrometer with MASSLYNX® 4.1 software.

Returning briefly to the separation means, the separation means may be selected from the solid phase extraction methods just described or liquid/liquid extraction or protein precipitation. In the event liquid/liquid extraction methods are preferred, the separation means comprises adding an aliphatic solvent to the aqueous solution comprising the supernatant. The aliphatic solvent and supernatant are mixed and separated to form an analyte solution.

As used herein, an aliphatic solvent is a comprised of organic molecules having one to twelve carbons. A preferred aliphatic solvent is hexane. Mixing is commonly performed by vortexing and the separation may be assisted by further centrifugation or merely allowing the aqueous and aliphatic media to separate and settle over time. The aqueous component is separated from the aliphatic component and forms the analyte solution.

In the event the separation means is protein precipitation, the separation means comprises adding a precipitating agent to the supernatant. The precipitating agent comprises concentrated salt solutions and/or alcohols, such as methanol, ethanol, propanol and butanol. The precipitating agents cause proteins to leave the supernatant by settling or further centrifugation to form the analyte solution.

Turning now to FIG. 1, a further embodiment of the present invention features a kit, generally designated by the numeral 11. The kit is for detecting the presence or absence of Vitamin D analogs in a sample comprising blood sera. The kit 11 has packaging 15 to hold the various parts, to be described in greater detail, comprising the assembly. Packaging 15 may comprise any number of forms such as a bag, plastic wrapping, plastic form or a box as depicted.

An effective amount of a multiple charge cationic agent is held in a vial 17. The vial 17 may contain the multiple charge cationic agent in solution or in a dry condition for reconstitution. One preferred multiple charge cationic agent is selected from the group comprising metal sulfate salts, such as zinc sulfate.

The kit further comprises instructions 19 for its use describing the method for determining the presence or absence or quantity of a vitamin D analog. In the method, an effective amount of a multiple charge cationic agent is added to the sample to form a cationic treated sample. The instructions 19 preferably describe the manner of for forming the multiple charge cationic agent.

In the event the sample is serum, the kit preferably comprises pipettes [not shown] for handling fluids. Kits directed to the analysis of solid tissue samples preferably comprise solutions or means for making solutions for solubilizing the tissues. For example, certain salts, known as chaotropic, dissolve cellular membranes. Such salts are contained in vials [not shown], in the manner of the multiple charge cationic agent, for being placed in solution.

One preferred kit 11 comprises separation means in the form of a preparatory chromatographic media, precipitating agent and/or liquid/liquid extraction materials and reagents. For example, the preparatory chromatographic media held in an extraction device, in the form of a multi-well plate or a preparatory column 21, is held in the packaging 15. A preparatory column 21 is depicted; however, a 96 well plate [not shown] may be preferred for some applications. The precipitating agents and/or liquid/liquid extraction materials and reagents are normally contained in vials or bottles [not shown].

Preferably, the kit comprises a known amount of a labeled vitamin D analog to facilitate quantification by mass spectroscopy. A preferred labeled vitamin D analog is selected from the group comprising deuterated vitamin D analogs. For example, if the analyte was 25(OH) Vitamin $D_3$ and 25(OH) Vitamin $D_2$, a preferred labeled vitamin D analog would comprise deuterated 25(OH) Vitamin $D_3$ and deuterated 25(OH) Vitamin $D_2$. Such labeled vitamin D analog, for dissolving in a suitable solvent, is shown as contained in vial 23. Instructions 19 describe the manner of its reconstitution.

The kit further comprises an analytical chromatographic media in the form of an analytical column 25.

Embodiments of the present invention are further exemplified in the following examples which highlight the detection and determination of concentration of 25(OH) Vitamin $D_2$ and $D_3$.

EXAMPLE

Example 1 and 2 will use the instruments, materials, settings and procedures described below:

Instrumentation

Mass spectrometer: WATERS® TQD S/N QBA068

Chromatography system: ACQUITY® HPLC® Chromatography system SM: S/N K06UPS15M (FW 1.23.172), BSM: S/N B07UPB805M (FW 1.23.121) Software: MassLynx 4.1

Materials and Methods

Standards 1 mg of 25 (OH) Vitamin D3 was purchased from Fluka (17938) and dissolved in 1 mL of ethanol. 1 mg of 25 (OH) Vitamin D2 was purchased from Fluka (17937) and dissolved in 1 mL of ethanol. d6-25(OH)Vit D3 is used as the internal standard. 1 mg was dissolved in 1 mL of EtOH to give a 1 mg/mL standard.

The 1 mg/mL stds were stored at −20 until required. The stds were diluted into the appropriate as solvent as required.

Example 1

Chromatography
Mobile phase A: Water with 2 mM ammonium acetate+ 0.1% formic acid
Mobile Phase B: MeOH with 2 mM ammonium acetate+ 0.1% formic acid
Weak wash solvent: Mobile phase A
Strong wash solvent: Mobile phase B
Column: Acquity BEH 2.1×50 mm C8 1.7 μm
Column temp: 45° C.
Injection Vol: 20 μL (PLNO, 50 μL loop and 250 μL sample syringe fitted)
Flow Rate: 0.35 mL/min
Gradient:

| Time | % A | % B | curve |
|---|---|---|---|
| 0 | 27 | 73 | 1 |
| 2 | 27 | 73 | 6 |
| 3.5 | 2 | 98 | 6 |
| 4.0 | 2 | 98 | 6 |
| 4.1 | 27 | 73 | 6 |

Run time: 6.0 mins

Mass Spectrometer (MS/MS)
The instrument was tuned for unit resolution for MS1 (0.7 Da HH) and the resolution for MS2 (0.9 Da HH).

| Polarity | ES+ |
|---|---|
| Capillary (kV) | 2.00 |
| Cone (V) | 22.00 |
| Extractor (V) | 3.00 |
| RF (V) | 0.1 |
| Source Temperature (° C.) | 120 |
| Desolvation Temperature (° C.) | 350 |
| Cone Gas Flow (L/Hr) | 50 |
| Desolvation Gas Flow (L/Hr) | 900 |
| Collision Gas Flow (mL/min) | 0.15 |
| LM 1 Resolution | 14.9 |
| HM 1 Resolution | 14.9 |
| Ion Energy 1 | 0.1 |
| MS Mode Entrance | 50.00 |
| MS Mode Collision Energy | 2.00 |
| MS Mode Exit | 50.00 |
| MSMS Mode Entrance | 0.00 |
| MSMS Mode Collision Energy | 12.00 |
| MSMS Mode Exit | 0.50 |
| LM 2 Resolution | 13.5 |
| HM 2 Resolution | 13.5 |
| Ion Energy 2 | 1.0 |
| Gain | 1.00 |
| Multiplier | −652.10 |

MRM Transitions

TABLE 2

MRM transitions for the analysis of 25(OH) Vit D2 and D3 and the d6 Vit D3 IS

| Compound | MRM | Dwell (secs) | Cone Voltage (V) | Collision Energy (eV) |
|---|---|---|---|---|
| 25-OH D3 | 401.2 > 159.1 | 0.05 | 22 | 28 |
| D6-25-OH D3 | 407.2 > 159.1 | 0.05 | 22 | 28 |
| 25-OH D2 | 413.15 > 83.15 | 0.05 | 30 | 22 |

Interscan Scan Delay (secs): 0.02
Interscan Channel Delay (secs): 0.01
Sample Extraction
Protein precipitation
150 μL serum
Add 10 μL IS 250 ng/mL d6-25(OH)Vit D3 (MeOH/IPA)
Vortex 5 secs,
Add 150 μL 0.2M ZnSO4
Vortex 5 secs
Add 600 μL MeOH
Vortex 30 secs
Centrifuge 13,000 rpm for 5 mins
Inject 20 μL supernatant
Liquid-Liquid Extraction
150 μL serum
Add 10 μL IS 250 ng/mL d6-25(OH)Vit D3 (MeOH/IPA)
Add 150 μL 0.2M ZnSO4
Vortex 5 secs
Add 300 μL MeOH
Vortex 5 secs,
Add 750 μL hexane
Vortex 30 secs,
Centrifuge 13,000 rpm for 5 mins
Remove top organic layer (hexane)
Dry down under nitrogen at 50° C.
Reconstitute in 75 μL 70/30 MeOH/water
Inject 20 μL
Solid phase extraction
Oasis HLB 30 mg 96 well plate
Sample pretreatment: 200 μL serum+10 μL IS (Xng/mL d6-25(OH)Vit D3 in 80/20 MeOH/IPA) vortex 5 secs+200 μL 0.2M ZnSO4 vortex 5 secs. Add 800 μL MeOH vortex 30 secs. Centrifuge for 5 mins at 13,000 rpm.
Condition 1: 1 mL ethyl acetate
Condition 2: 1 mL MeOH
Equilibration: 1 mL water
Load: supernatant
Wash 1: 1 mL 5% MeOH
Wash 2: 1 mL 80% MeOH
Elute: 2×500 μL ethyl acetate
Dry down under nitrogen at 50° C., reconstitute with 100 μL of 70/30 MeOH/Water.
Inject 20 μL on column Example 2

25(OH) Vitamin $D_2$ and $D_3$ Analysis
SPE/HPLC/MS/MS conditions
Chromatography
Mobile phase A: Water with 2 mM ammonium acetate+ 0.1% formic acid
Mobile Phase B: MeOH with 2 mM ammonium acetate+ 0.1% formic acid
Weak wash solvent: Mobile phase A, 600 μL
Strong wash solvent: Mobile phase B, 200 μL
Seal Wash: 20% MeOH aq
Column: ACQUITY BEH 2.1×50 mm Phenyl 1.7 μm (P/N 186002884) with pre-column filter
Column temp: 60° C.
Injection Vol: 20 μL (PLNO, 50 μL loop and 250 μL sample syringe fitted) 3 μL overfill (SCN 627), load ahead
Flow Rate: 0.4 mL/min Gradient:

| Time | % A | % B | curve |
|------|-----|-----|-------|
| 0    | 35  | 65  | 1     |
| 2.5  | 15  | 85  | 6     |
| 2.6  | 2   | 98  | 6     |
| 3.1  | 35  | 65  | 11    |

Run time: 4.0 mins

Mass Spectrometry

The instrument was tuned for unit resolution for MS1 (0.7 Da FWHM) and the resolution for MS2 (0.8-0.9 Da FWHM).

| MS Conditions | |
|---|---|
| Polarity | ES+ |
| Capillary (kV) | 2.5 |
| Cone (V) | 24.00 |
| Extractor (V) | 3.00 |
| RF (V) | 0.1 |
| Source Temperature (° C.) | 120 |
| Desolvation Temperature (° C.) | 350 |
| Cone Gas Flow (L/Hr) | 50 |
| Desolvation Gas Flow (L/Hr) | 900 |
| Collision Gas Flow (mL/min) | 0.15 |
| LM 1 Resolution | 14.9 |
| HM 1 Resolution | 14.9 |
| Ion Energy 1 | 0.1 |
| MSMS Mode Entrance | 0.00 |
| MSMS Mode Collision Energy | 12.00 |
| MSMS Mode Exit | 0.50 |
| LM 2 Resolution | 13.5 |
| HM 2 Resolution | 13.5 |
| Ion Energy 2 | 1.0 |

MRM Transitions

| Compound | MRM | Dwell (secs) | Cone Voltage (V) | Collision Energy (eV) |
|---|---|---|---|---|
| 25(OH) $D_3$ | 401.35 > 159.1 | 0.02 | 24 | 28 |
| 25(OH) $D_3$ | 401.35 > 365.35 | 0.02 | 24 | 12 |
| $d_6$-25(OH) $D_3$ | 407.35 > 159.1 | 0.02 | 24 | 28 |
| 25(OH) $D_2$ | 413.35 > 83.1 | 0.02 | 24 | 24 |
| 25(OH) $D_2$ | 413.35 > 355.35 | 0.02 | 24 | 10 |

MRM transitions for the analysis of 25(OH) Vit $D_2$ and $D_3$ and the $d_6$ Vit $D_3$ IS, transitions in red are optional qualifier ions.

Interscan Scan Delay (secs):0.02
Interscan Channel Delay (secs):0.01
Oasis® HLB pElution SPE Extraction This SPE extraction step features an 96 well devices with a organic polymer sorbent with hydrophilic lipophilic balance cold under the trademark OASIS® (Waters Corporation, Milford, Mass. USA).

Sample Preparation:
Add 150 µL of serum to a 2 mL deep well 96 well-plate
Add 20 µL IS: 250 ng/mL $d_6$-25(OH)Vit $D_3$ (60% MeOH/40% IPA)
Vortex 10 secs
Add 150 µL 0.2M $ZnSO_4$ aq
Vortex 10 secs
Add 600 µL MeOH
Vortex 30 secs,
Centrifuge plate 13,000 rpm for 5 mins
Remove 600 µL of the supernatant and use a for the load step.

SPE Oasis® HLB pElution (P/N 186001828BA) Protocol:
Conditioning: 200 ul Methanol
Equilibration: 200 ul 60% Methanol (aq)
Load Sample: 600 ul of supernatant from above sample preparation.
Wash 1: 200 ul 5% Methanol (aq)
Wash 2: 200 ul 60% Methanol (aq)
Elution 1: 80 ul 60/40 Methanol/IPA
Elution 2: 40 ul Water®.
(Elute into Waters®1 ml 96 Well-Plate)
Mix plate well (Vortex for 180 secs)
Inject 20 µL on column Thus, embodiments of the present invention have been described with the understanding that the invention can be altered and modified without departing from the teaching herein. Therefore, the invention should not be limited to the precise details but should encompass the subject matter of the claims that follow and their equivalents.

What is claimed:

1. A method for detecting the presence or absence of Vitamin D analogs in a sample comprising the steps of:
    adding an effective amount of a multiple charge cationic agent to said sample to form a cationic treated sample, said effective amount of said multiple charge cationic agent enhancing the signal from Vitamin D analogs upon further analysis by mass spectroscopy;
    subjecting said cationic treated sample to centrifugation to form a supernatant;
    separating proteins in said supernatant from said Vitamin D analogs by protein precipitation to form an analyte solution;
    placing said analyte solution on an analytical column and forming a eluent having said Vitamin D analogs separated from each other and non-Vitamin D compounds,
    placing said eluent in a mass spectrometer and detecting the presence or absence of Vitamin D analogs in the sample by mass spectra.

2. The method of claim 1 wherein said protein precipitation comprises mixing a precipitating agent with said supernatant and separating said protein from the supernatant to form said analyte solution.

3. The method of claim 2 wherein said protein is separated by centrifugation.

4. The method of claim 1 wherein said sample is serum.

5. The method of claim 1 wherein said multiple charge cationic agent is selected from the group consisting of metal sulfate salts.

6. The method of claim 1 wherein said metal sulfate salt is zinc sulfate.

7. The method of claim 1 further comprising adding a known amount of a labeled Vitamin D analog to said sample.

8. The method of claim 7 wherein said labeled Vitamin D analog is selected from the group consisting of deuterated 25(OH) Vitamin D3 and deuterated 25(OH) Vitamin D2.

9. The method of claim 1 wherein said analyte solution is dried and reconstituted in methanol and water prior to placing said analyte solution on the said analytical column.

10. A kit for detecting the presence or absence of Vitamin D analogs in a sample comprising:
    an effective amount of a multiple charge cationic agent, a protein precipitating agent, and instructions for use of said multiple charge cationic agent in a method to detect the presence or absence of Vitamin D analogs;
    said method comprising adding said effective amount of a multiple charge cationic agent to said sample to form a cationic treated sample, said effective amount of the multiple charge cationic agent enhancing the signal from Vitamin D analogs upon further analysis by mass spectroscopy; centrifuging said treated sample to form a supernatant, separating protein in said supernatant from said Vitamin D analogs by protein precipitation with said protein precipitating agent to form an analyte solution, placing said analyte solution on an analytical column and forming an eluent having said Vitamin D analogs separated from each other and non-Vitamin D compounds, and placing said eluent in a mass spectrometer and detecting the presence or absence of Vitamin D analogs in the sample by mass spectra.

11. The kit of claim 10 wherein said multiple charge cationic agent is selected from the group consisting of metal sulfate salts.

12. The kit of claim 10 wherein said metal sulfate salt is zinc sulfate.

13. The kit of claim 10 wherein said kit further comprises a known amount of a labeled Vitamin D analog to facilitate quantification by mass spectroscopy.

14. The kit of claim 13 wherein said labeled Vitamin D analog is selected from the group consisting of deuterated 25(OH) Vitamin D3 and deuterated 25(OH) Vitamin D2.

15. The kit of claim 10 further comprising an analytical column.

16. The kit of claim 15 wherein said analytical column has a chromatographic media comprising a bridged ethyl hybrid material.

17. The kit method of claim 10 wherein said protein precipitating agent comprises a concentrated salt solution or an alcohol.

\* \* \* \* \*